United States Patent
Leydet et al.

(10) Patent No.: US 8,298,293 B2
(45) Date of Patent: Oct. 30, 2012

(54) PROSTHETIC SENSING SYSTEMS AND METHODS

(75) Inventors: Michael G. Leydet, St. Clair Shores, MI (US); Richard H. Harrington, Dexter, MI (US); Frank J. Fedel, Dearborn Heights, MI (US); Michael Link, Chesterfield, MI (US); Joshua J. Street, Livonia, MI (US)

(73) Assignee: College Park Industries, Inc., Fraser, MI (US)

( * ) Notice: Subject to any disclaimer, the term of this patent is extended or adjusted under 35 U.S.C. 154(b) by 915 days.

(21) Appl. No.: 11/741,397

(22) Filed: Apr. 27, 2007

(65) Prior Publication Data
US 2007/0255424 A1 Nov. 1, 2007

Related U.S. Application Data

(66) Substitute for application No. 60/796,301, filed on Apr. 28, 2006.

(51) Int. Cl.
*A61F 2/70* (2006.01)
(52) U.S. Cl. ........................................................ 623/24
(58) Field of Classification Search .................... 623/24, 623/912
See application file for complete search history.

(56) References Cited

U.S. PATENT DOCUMENTS

| | | | | |
|---|---|---|---|---|
| 5,201,772 A | * | 4/1993 | Maxwell | 623/24 |
| 5,253,656 A | * | 10/1993 | Rincoe et al. | 600/595 |
| 6,871,552 B2 | | 3/2005 | Liu et al. | |
| 7,455,696 B2 | | 11/2008 | Bisbee, III et al. | |
| 7,500,407 B2 | * | 3/2009 | Boiten | 73/862.191 |
| 2005/0107889 A1 | * | 5/2005 | Bedard et al. | 623/24 |

FOREIGN PATENT DOCUMENTS

SU 1621914 A1 * 1/1991
WO WO-9641599 12/1996

OTHER PUBLICATIONS

English translation of SU 1621914 A1.*

* cited by examiner

*Primary Examiner* — David H. Willse
(74) *Attorney, Agent, or Firm* — Gifford, Krass, Sprinkle, Anderson & Citkowski, P.C.

(57) ABSTRACT

Systems and methods are disclosed for sensing forces, moments, temperature, inclination, acceleration and other parameters associated with prosthetic limbs. The system is capable of measuring forces in three designated axes, and moments about the same designated axes, for a total of six possible degrees of freedom. The system can be readily fitted onto a conventional prosthetic limb with no, or relatively minor, modification thereto. A plurality of sensor arrays are disposed on a support member, each array including a plurality of strain gauge sensors, each sensor outputting an electrical signal responsive to loading imposed on the support member through the prosthetic limb. Electronic circuitry in communication with the gauges is operative to receive the electrical signals from the strain gauges and provide a signal useful in the form, fit or function of the prosthetic limb.

7 Claims, 4 Drawing Sheets

PROSTHETIC SENSING SYSTEMS AND METHODS

REFERENCE TO RELATED APPLICATION

This application claims priority of U.S. Provisional Patent Application Ser. No. 60/796,301, filed Apr. 28, 2006, the entire content of which is incorporated herein by reference.

FIELD OF THE INVENTION

This invention relates to systems and methods for sensing forces, moments, temperature, inclination, acceleration and other parameters associated with prosthetic limbs. More specifically, the invention relates to systems capable of measuring forces in three designated axes, and moments about the same designated axes, for a total of six possible degrees of freedom that can be associated to the object in three-dimensional space.

BACKGROUND OF THE INVENTION

It is often desirable to measure stresses and strains caused by loads or loading which occur in the use of prosthetic limbs. It may also be desirable to measure the inclination and acceleration of the prosthesis which are also critical to promote better gait. Such measurement may be made in connection with the design of prosthetic limb systems or with the fitting or adjustment of limbs, or the analysis of the user's motion in the course of operating a limb, as for example in the case of gait analysis. In other instances, loads may be measured or detected as part of an alarm system which indicates malfunction in a prosthetic limb. In yet other instances, such measurements may be used to control the operation of a component of a limb such as a motion damper, an electronically controllable joint, or other such structure.

In response to needs and applications such as the aforedescribed, the prior art has implemented various approaches to systems for measuring loads in prosthetic limbs. Some measurement systems rely upon the use of devices external to the limbs such as pressure plates and the like. Such systems are often difficult to use, and can interfere with a normal range of motion by the user; furthermore, such systems generally provide relatively limited data. Various onboard systems have been implemented; however, such systems generally require significant modification of a prosthetic limb. Hence they are not readily utilizable in connection with diagnosis of persons using preexisting limb systems. Furthermore, their complexity generally restricts their use to dedicated research applications.

SUMMARY OF THE INVENTION

This invention relates to systems and methods for sensing forces, moments, temperature, inclination, acceleration and other parameters associated with prosthetic limbs. In the preferred embodiment the system is capable of measuring forces in three designated axes, and moments about the same designated axes, for a total of six possible degrees of freedom.

The system comprises a plurality of sensor arrays disposed on a support member, each array including a plurality of strain gauge sensors, each sensor outputting an electrical signal responsive to loading imposed on the support member through the prosthetic limb. Electronic circuitry in communication with the gauges is operative to receive the electrical signals from the strain gauges and provide a signal useful in the form, fit or function of the prosthetic limb.

In accord with the preferred embodiment, each strain gauge array includes a plurality of strain gauge sensors oriented to sense loads along three independent axes and the moments associated therewith so as to determine all six subcomponents needed to fully describe a load applied to the prosthetic limb. In one disclosed configuration for accomplishing this, the gauges of the array include an axially oriented gauge and a pair of gauges oriented at angles such as +/−45 degrees on either side of the axially oriented gauge.

The support member may be a flexible panel or a rigid tube having a first end configured for attachment to the socket of a prosthetic limb, and a second end configured for attachment to a pylon of a prosthetic limb. If used with a prosthetic leg, for example, the support member may be placed between the foot and a pylon, between the pylon and a knee device, above a knee device, or between a knee device and an above-the-knee socket.

The electronic circuitry may be configured so that the strain gauges generate positive and negative (signed) voltages. This allows the circuitry to determine moments and shear forces based upon the signed voltages generated by the strain gauges, providing the ability to compensate for off-center loading. Analog or digital switches may be provided to activate the strain gauges as necessary to conserve power or reduce heat generation. An analog multiplexer may be provided to interconnect the strain gauges to a common instrumentation amplifier such that the gains of the strain gages are substantially equalized.

In addition to the strain gauges, the system may receive inputs from an inclinometer and accelerometer, in which case the signal provided by the electronic circuitry may be used to analyze the gait of a user. A pair of inclinometers may be provided, one disposed on either side of an articulating joint such as an ankle joint, in which case the electronic circuitry is operative to receive signals from the inclinometers and output data approximating a goiniometer.

To enhance versatility, the system may include a data collection module for receiving the signal from the electronic circuitry. The module may be remotely located and may communicate with the electronic circuitry through a wired or wireless connection. In addition to the affected limb system, the module may receive signals from an unaffected limb electronics package including an inclinometer or accelerometer, in which case the module may analyze a more complex gait pattern. The unaffected limb electronics package may also include a pair of inclinometers to implement a goiniometer function associated with the unaffected limb.

The may be powered by a generator associated with said prosthetic limb such as a piezoelectric generator or a moving magnet generator. The electronic circuitry may operate on an intermittent basis so as to conserve power. A motion detector may be provided such that when motion is detected, operation of the electronic circuitry is initiated.

The data provided by the electronic circuitry may be used for a variety of purposes. For example, it may be used to control a component of the prosthetic limb or provide an alarm indicating malfunction of the prosthetic limb. A method of analyzing the gait of a user includes the steps of disposing the system on a prosthetic leg or arm worn by the user, having the user walk, and analyzing the signal provided by the electronic circuitry. Other methods are disclosed, including methods of controlling the operation of an electronically controllable component associated with the prosthetic limb.

DETAILED DESCRIPTION OF THE PREFERRED EMBODIMENTS

This invention relates to systems and methods for sensing forces, moments, temperature, inclination, acceleration and other parameters associated with prosthetic limbs. The preferred embodiments are capable of measuring forces relative to three designated axes, and moments about the same designated axes, for a total of six possible degrees of freedom associated with the object in three-dimensional space. The invention is applicable to legs and arms, with amputation or deficiency occurring at any point facilitating a workable coupling. In all cases a goal is to provide a sensing system that attaches to a prosthetic limb with no, or relatively minor, modification thereto.

One disclosed embodiment includes a support member to which a plurality of strain gauge sensors are affixed in a preselected pattern. Each strain gauge is operative to provide a change in one of its detectable characteristics, typically electrical resistance, in response to a strain imposed on the member. The system further includes an electronics package which is in communication with the gauges. The electronics package is operative to detect the change in detectable characteristics of the strain gauges and to provide data in response thereto, such data being useful in the form, fit or function of the prosthetic limb.

The sensing system may replace a support member of the prosthetic limb with an Intelligent Tube Clamp Adapter (ITCA). Alternatively, the system may be integrated to an existing prosthetic component. The support member may be rigid, semi-rigid, or may comprise a body of flexible material such as a polymeric sheet which may be affixed to the limb, for example, by the use of an adhesive. The electronics package may be mounted either on the support member or on the limb itself. As explained in greater detail herein, the electronics package may be operative to process and/or store sensor signals, and in some instances, communicate them via a wired or wireless link to a computer or data collection module (DM). The DCM may also receive signals from an unaffected limb electronics package (ULEP) according to the invention to form an intelligent prosthetic endo component system (IPECS) providing, among other functions, a virtual goiniometer capability.

Figure 1:
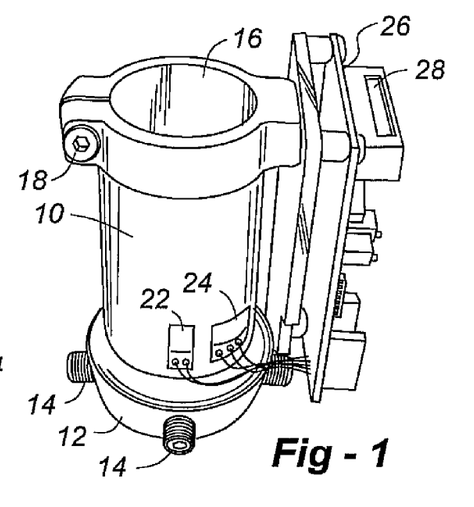
FIG. 1 is a front view of a system optimized for use with a prosthetic leg according to the invention.
Figure 2:
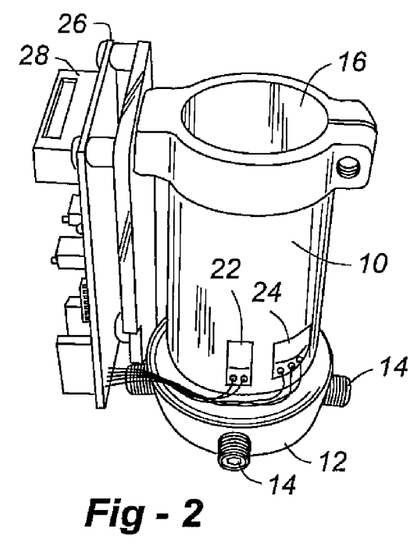
FIG. 2 is a back view of a system optimized for use with a prosthetic leg according to the invention.

FIGS. 1 and 2 are respective front and back views of one specific embodiment of the invention. As shown, the device includes a support member 10, which in this instance is a rigid housing configured for attachment to a prosthetic limb. The housing is configured so that a first end 12 is affixable to the socket portion of a prosthetic limb via set screws 14. A second end 16 is configured to clamp onto a pylon portion of the limb, and as such includes a split sidewall operative in cooperation with a screw 18. As shown in these drawings, the support member 10 is configured to clamp onto a pylon having a circular cross section. It is to be understood that the support member 10 may likewise engage a pylon having another configuration of cross section, such as an oval cross section, a polygonal cross section or an irregular cross section.

In the use of the system of FIGS. 1 and 2, the housing 10 is joined to the socket portion of the prosthetic limb, which socket portion engages the stump of the limb. In the case of a leg prosthesis, the pylon has a prosthetic foot joined to the second end 16. In those instances where the user is an above-the-knee amputee, an artificial knee joint mechanism may be included in the assembly, and the sensor of the present invention is typically incorporated in the below the knee joint portion; although, in some applications, it may alternatively be disposed above the knee joint.

The system illustrated in FIGS. 1 and 2 may be readily incorporated into a pylon of a prosthetic limb with minor modification. The housing is configured so that the first end 12 fits onto a conventional socket in a similar manner to a typical pylon connection. Therefore, no modification of the socket need be carried out. The second end of the housing is configured to fit onto a standard pylon, and again no modification is needed. The housing itself will occupy some length of the limb, and typically the length of the pylon will be adjusted to accommodate for the length of the housing. If it is desired to remove the system after measurements have been made, a conventional pylon of standard length may be substituted for the shortened pylon, and the prosthetic limb returned to use with no further modification being required.

The sensor system includes a plurality of strain gauges which are, in this embodiment, affixed to the housing, and in FIGS. 1 and 2, two of these strain gauges 22, 24 are shown. The housing may have markings thereupon to aid in the proper placement of the strain gauges 22, 24. Although not visible in these figures, further strain gauges may be incorporated onto the housing 10 as described elsewhere herein. In the illustrated embodiment, the electronics package is disposed on a circuit board 26 affixed to the housing. The housing includes a connector 28 that allows the electronics package to be in communication with another electronic device such as a data processor, mass data storage device or the like. This other device may be disposed on the limb or off the limb as described in further detail herein.

As is known in the art, the strain gauges may be adhesively affixed to the ITCA or, as for example, to the pylon. After affixation, the strain gauges may be adjusted by physical calibration processes such as laser trimming; alternatively, dynamic calibration processes, implemented through software and/or hardware in the electronics package, may be used to accommodate variations in sensor response and/or sensor placement. A dynamic trimming procedure is described in further detail herein below.

Figure 3:
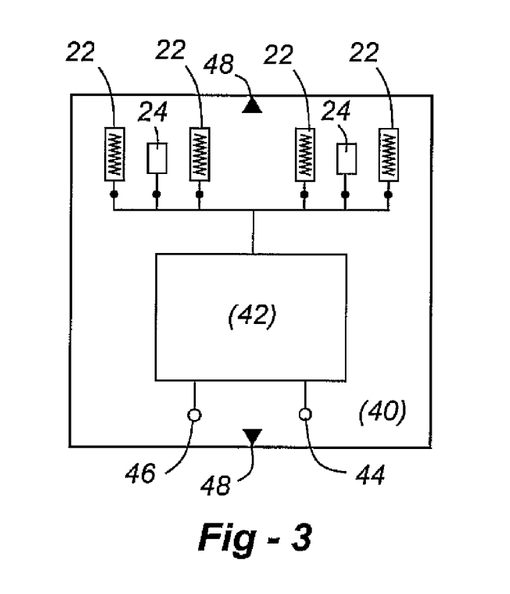
FIG. 3 shows an embodiment of the invention in which a relatively flexible support member for sensors and an electronics package.

While embodiments of the invention position the strain gauges and electronics package onto a relatively rigid member which is coupled to a prosthetic limb system, other embodiments of the present invention are contemplated. For example, FIG. 3 shows an embodiment of the invention in which a relatively flexible support member 40 supports the sensors and electronics package. The support member 40 is generally made from a polymeric material of the type used for flexible printed circuit boards, and such material includes polyimide polymers such as Kapton®, polyesters, polysulfones, polyethers, and other relatively stable, flexible polymers. Disposed upon the flexible member 40 are strain gauges, which in this instance are similar to the strain gauges 22 and 24 previously described. Also included is an electronics package 42 which is in communication with the sensors.

As illustrated in FIG. 3, the electronics package includes terminals 44, 46 associated therewith, and these terminals, as well as further terminals, may be used to establish connection to the electronics package for data transfer, power supply and the like. Circuitry for the electronics package may be formed directly on the support member 40, and techniques such as chip onboard technology may be utilized as is known in the art.

In the use of the system of FIG. 3, the flexible support member 40 is mounted onto a portion of a prosthetic limb, such as the pylon or other portions of limb structures. Mounting is typically accomplished by the use of an adhesive material, and adhesives which form a rigid bond are generally favored so that transfer of limb loading is efficiently accomplished. Such adhesives may include curable adhesives such as epoxies, urethanes and the like. To aid in alignment of the sensing system on the prosthetic limb, alignment markings such as markings 48 are included on the substrate 40.

Figure 4:
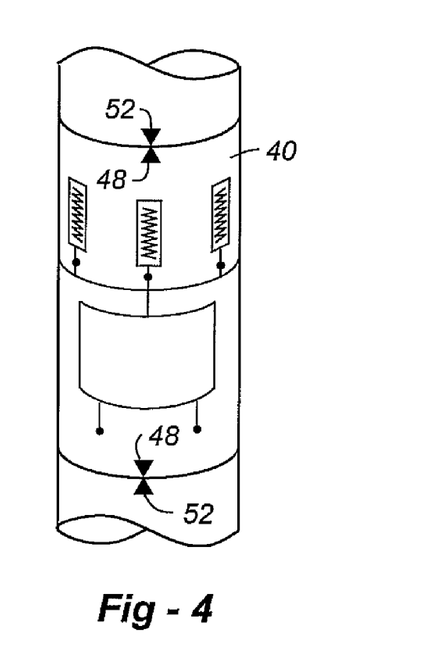
FIG. 4 shows a portion of a prosthetic limb, in this instance a pylon, having the flexible support mounted thereupon.
Figures 5, 6, 7:
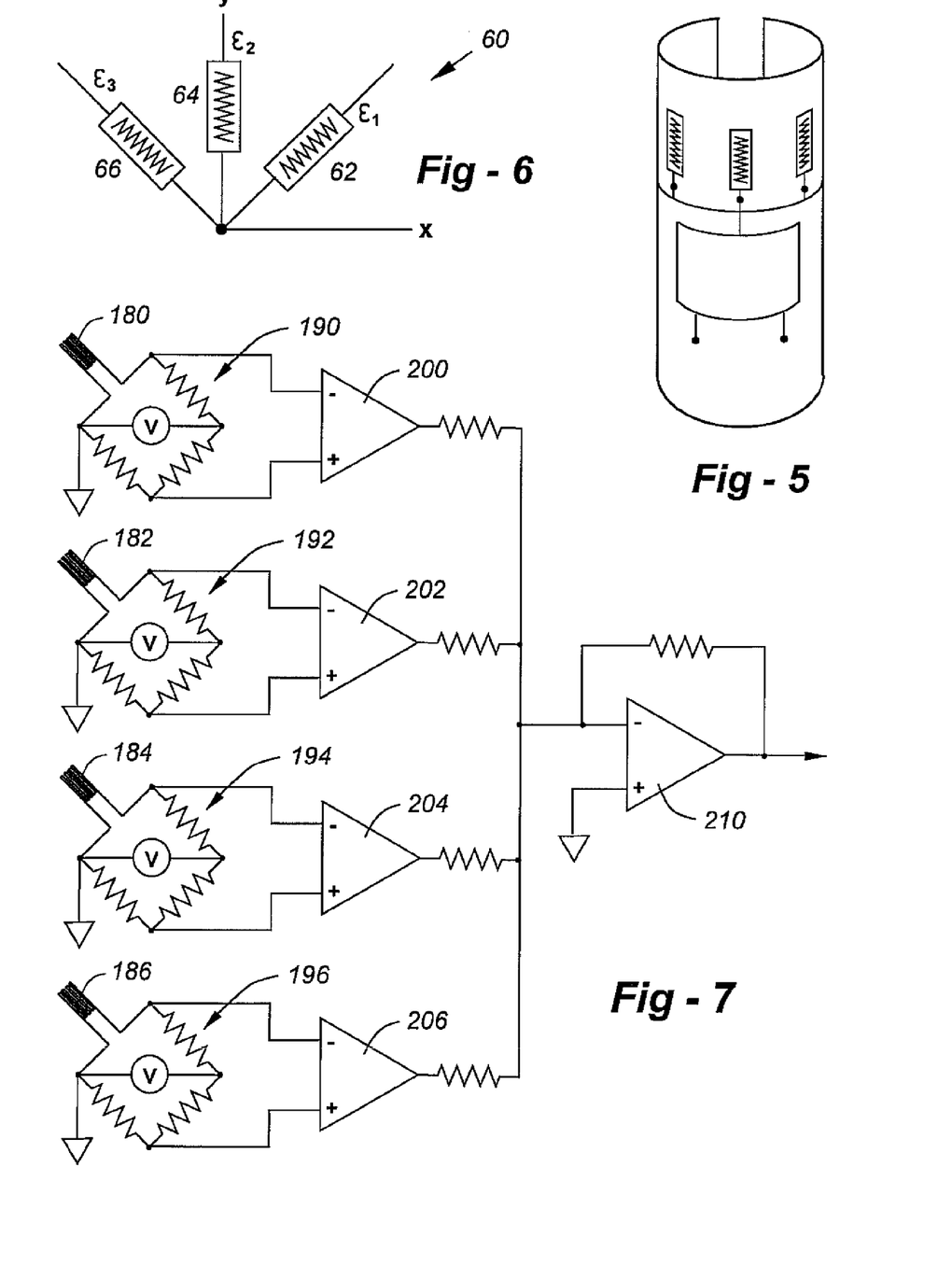
FIG. 5 shows a sensing system wherein the flexible substrate portion is formed into a cylinder.
FIG. 6 shows a rosette strain gauge array comprising three strain sensors sensitive to strains along three axes.
FIG. 7 shows four instrumentation amplifiers, one associated with a bridge configuration, the outputs of which are summed by an operational amplifier.

FIG. 4 shows a portion of a prosthetic limb, in this instance a pylon having the flexible support 40 mounted thereupon. As will be noted, the alignment marks 48 on the flexible member 40 are aligned with corresponding marks 52 on the pylon. In some instances it may be advantageous to preform the sensing system so as to conform to the substrate upon which it will be disposed. FIG. 5 shows a sensing system wherein the flexible substrate portion 40 is formed into a cylinder. Other such preformed shapes will also be apparent to those of skill in the art.

Different types of strain gauges may be used according to the invention. Gauges 22, for example, are unidirectional gauges disposed so as to measure loading in the X and Y (horizontal) axis of the limb when it is in use. Diametrically opposed strain gauges 24, each include two strain variable resistors and each forms a full Wheatstone bridge. In this embodiment, these paired gauges are used to measure loading in the Z axis, which is generally aligned with the length axis of the prosthetic limb.

In the preferred embodiment, however, all of the strain gauges are rosette strain gauge arrays comprised of at least three strain sensors. In this manner, each of the arrays will be sensitive to strains along three axes. One such gauge is shown in FIG. 6 at reference numeral 60. This gauge 60 includes three resistive components 62, 64 and 66, and is mounted on the prosthetic limb so that the direction of strain gauge 64 is generally parallel to the Z axis for the highest sensitivity. At least two other gauge elements, 62, 66 are placed on either side of element 64 and oriented for the highest sensitivity orientations of 45 degrees and −45 degrees off-axis, respectively. Other gauge clusters are similarly disposed about the ITCA. Using an arrangement as described, normal strain as measured by the gauge at a given point can be translated into shear strain at the same location utilizing the following equation:

$$\gamma_{xy} = \epsilon_1 - \epsilon_3$$

where $\epsilon_1$ is the strain sensed by element 64 and $\epsilon_3$ is the strain sensed by element 62.

Utilizing strain gauge arrangements of the types described above, it is possible to represent direct relationships between normal strain and contributing force and moment components of applied loads. Therefore, by the use of appropriately positioned strain gauges, it is possible to determine all six subcomponents needed to fully describe an applied load on a prosthetic limb. Systems of this type may be adapted to regular structures such as circular pylons, as well as to structures having noncircular but symmetrical cross sections, particularly if consistent circumferential placement is used.

Different placements of the gauges afford certain advantages. For example, strain gauges spaced equidistantly from the centroid of the loaded member facilitates off-center load rejection. According to this embodiment, four strain gauges are placed on the tube to measure X and Y bending forces. These gauges are placed at 0 degrees, 180 degrees for the Y bending force, and at 90 and 270 degrees to measure the X bending force. To handle the addition and subtraction of strain values each gauge subcomponent 180, 182, 184, 186 is in a quarter Wheatstone bridge setup 190, 192, 194, 196 as shown in FIG. 7. A microprocessor associated with the electronics portion of the system handles the necessary mathematics.

The accepted method for transducer applications typically use half or full Wheatstone bridge configurations to measure strain. The benefits include automatic temperature compensation and improved signal-to-noise ratio. For example, a conventional approach is to use two T-rosette gauges in a fill Wheatstone bridge configuration. The gauges typically have two gauge patterns that are perpendicular to each other. The gauges are typically placed with one gauge pattern along the Z axis and the other along the X axis. The gauge in the X axis senses the Poisson's strain which is very small compared to the axial strain, typically about 3% of the axial strain and is used for temperature compensation.

When an on-center load is applied to the end of the tube (Z axis), the two axial gauges of the 2 T-rosette gauges will be in compression, and when used in the standard Wheatstone bridge configuration, the full bridge which uses all elements of two T-rosette gauges will produce a voltage proportional to the applied force. However, when an off-center force is applied, an error occurs. The reason for the error arises from the way in which the bridge is set up, in that signed numbers are not taken into account. As such, the full Wheatstone bridge using axial and lateral gauges does not perform the proper math to give correct off-center load results.

An alternative approach is to use a different bridge configuration using four gauges and summing the signed result. When an off-center load is applied to the column, the gauges applied to the same side of the column will be in compression and gauges opposed to the ones in compression will be in tension. The proposed strain gauge circuit provides a negative voltage for compression, a positive voltage for tension and then when summed together, they produce a result consistent with the applied load. The summation can be done in an analog fashion using a summing operational amplifier, or more complex calculations can be done with a computer after an A/D conversion is done.

Figure 8:
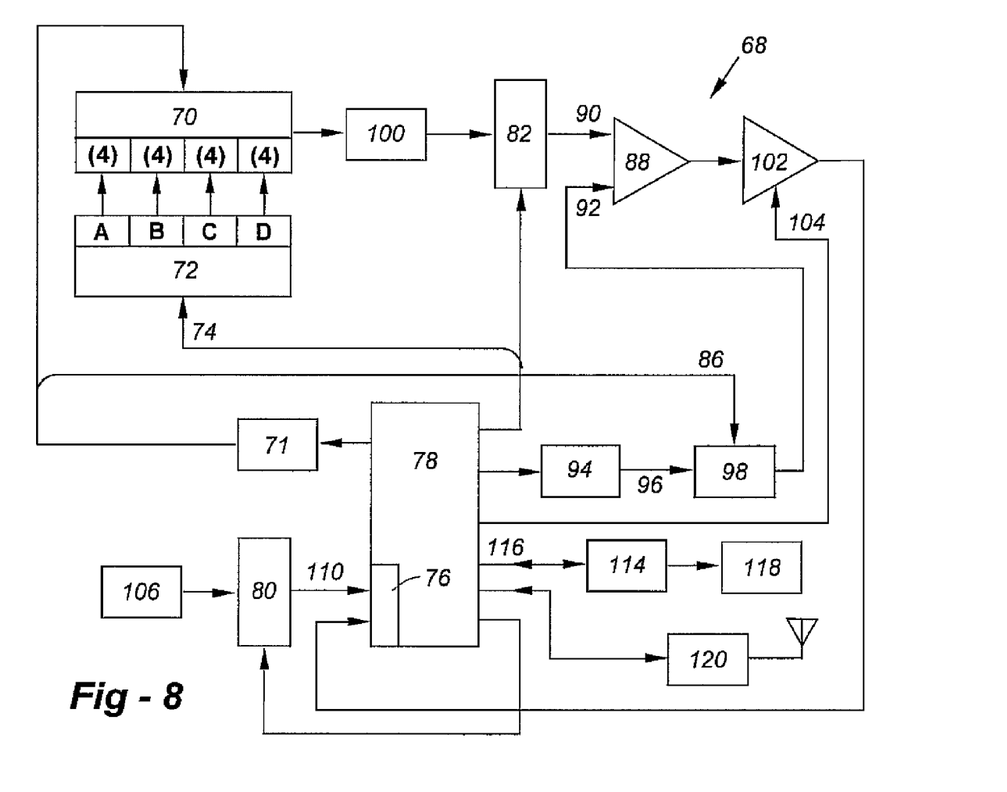
FIG. 8 is a block diagram of an electronics package for an intelligent tube clamp adapter (ITCA) according to the invention.

Referring again to FIG. 7, four instrumentation amplifiers 200, 202, 204, 206, one associated with each bridge configuration, provide outputs which are summed by operational amplifier 210. Alternatively, as shown in FIG. 8, one instrumentation amp may be used if the outputs of the bridges are multiplexed under microprocessor control. After performing the A/D conversion of the gauges, an algebraic addition can be used to solve for the Z axis. Since only one instrumentation amp is used, the error in that amp will be the same for all readings, and if a precision reference and ground are provided to the multiplexer, the absolute value from the gauges may be determined with the instrumentation amp gain error being removed from the error equation.

An additional benefit of multiplexing is automatic temperature compensation. If all strain gauges track with temperature, for instance the resistance of the gauges rises by the same amount with an increase in temperature, the net result as seen by the A/D converter will be same for all the gauges. The instrumentation amp is a differential amplifier and only amplifies the difference in the strain gauge resistances, so the instrumentation amp output will not change. In FIG. 8, signal 92 is one of the two inputs to the instrumentation amp. This signal is the strain gauge excitation voltage divided by two plus an offset calculated by the microprocessor to make this voltage compatible with the strain gauge that is being selected by the multiplexer.

With four gauges at 0, 90, 180 and 270 degrees, the electronics package can be used to solve X moments and Y bending moments. The math for solving X and Y bending is to reverse the sign of one of the X or Y measurements and then add the two values together. The sign reversal is necessary because with an on-center load application, to X and Y outputs would both be positive and in proportion to the applied force. Reversing the sign of one of the gauges and then adding corrects the problem. Zero output at on center loading and either negative or positive depending on force application, such that with four gauges, Z axial and X and Y moments may be determined. Additional gauges may also be multiplexed into the same instrumentation amplifier.

Calibration of the load cell can be accomplished using an automated process, applying known forces, and performing the gain correction and zero correction using the embedded micro in the load cell. However, more often than not, small adjustments to the bridge resistors are necessary to produce a voltage that will not cause the associated instrumentation amplifier to go into saturation, or not be within the working range of the analog-to-digital (A/D) converter. The overall gain of the instrumentation amplifier block is often 1,000 or more, and the strain gauges are produced to a typical absolute resistance of 0.3% and the resistors that are in series with the gauges have a 0.1% tolerance. This tolerance stack-up will produce a 10 volt error after being amplified 1,000 times. This error must be reduced before it can go to the A/D.]

This dynamic trimming is used instead of having to add small resistance wire in series with the strain gauges so that the Wheatstone bridge can be balanced. The dynamic trimming is done in the following way: the microprocessor executes a routine that selects a strain gauge with no load and looks at the A/D voltage for that gauge. Using successive approximation, the processor calculates the proper off-set value for each gauge. These values will be stored in flash memory for use each time that gauge is being selected, and will be used by the DAC that produces the off-Set value. This voltage will force the voltage at the one of the instrumentation amplifier's inputs to a value that makes the input to the A/D converter in the working range.

Intelligent Tube Clamp Adapter (ITCA) Operation

The electronics package may be variously configured depending upon the particular application. In the embodiment of FIG. 8, 12 to 16 strain gauges 70 are bonded to the intelligent tube clamp adapter (ITCA), for measuring forces and moments. Each strain gauge has two resistors in series, which equal the strain gauge resistance. A group of four strain gauges and their corresponding resistors are tied to a common point, shown as blocks A, B, C, and D on the block diagram. These points are connected to power MOSFETS (also not shown), powered by programmable power supply 71. The power MOSFETS have a very low drain-source (D-S) ON resistance (120 m Ohms max). They should not effect the strain gauge measurement as long as the D-S ON resistance is accounted for during calibration. Block activation is used at 72 through SELECT lines 74 to save on power and reduce the self-heating of the ITCA by strain gauges. The strain gauge circuits draw 57 mA per block of 4 strain gauges/resistors. If all the strain gauges were on all the time, 228 mA would be needed and it would produce 1.7 Watts of power.

The A/D converter 76 located in the microprocessor 78 can only perform one conversion at a time, so an analog multiplexer 82 is provided to accommodate the large number of channels. The outputs of the strain gauges/resistors are connected to a 16-channel analog multiplexer which is addressed by the microprocessor 78 via path 84. The multiplexed voltages will be ~½ of the strain gauge excitation voltage. The strain gauge excitation voltage is controlled by the microprocessor by changing the voltage output on 68 and 86. The output of the 16-channel analog multiplexer 82 is fed to instrumentation amplifier on path 90 along with a signal on path 92 equal to ½ the strain gauge excitation voltage and a bias voltage which is controlled by the microprocessor. This bias voltage is produced by D/A converter 94. The offset on 96 is then fed to voltage divider and summer 98. The reason for this is that, more often than not, small adjustments to the bridge resistors are necessary to produce a voltage that will not cause the instrumentation amplifier to go into saturation. This improved method makes the small adjustments to the bridge resistors unnecessary, and will force the instrumentation amp output voltage to be in the working range of the A/D converter.

The strain gauges in this embodiment are arranged as 16, ¼-bridge configurations (100); however, in reality they form at a minimum a ½ bridge configuration. This is a very important fact because of the benefits obtained by the ½ or full bridge over that of a ¼ bridge. Consider two axial strain gauges located 180 degrees apart on the ITCA. The two gauges get transferred to a single instrumentation amplifier (which provides the added benefit that all the strain gauges can have the exactly the amplification factor applied) and then to programmable gain amplifier 102, which will be set to the same gain while looking at the two opposed gauges. The microprocessor performs mathematics on the various gauges to make a composite value. In the case of an on-axis load, the resultant output will be four times greater than a single ¼ bridge because there are four gauges used for this equation. If the four axial gauges were connected in the conventional full Wheatstone bridge, it would have zero output with on-center load because all the gauges would be at the same resistance, so the voltage going into the instrumentation amplifier would be zero.

Another benefit is automatic temperature compensation which is a considerable problem for a ¼ bridge. Using the multiplexer, a single instrumentation amplifier and programmable gain amplifier, temperature compensation will be accomplished (assuming the whole ITCA tube is at the same temperature) because the strain gauges will track each other with temperature. If one gauge goes up in resistance, the opposing gauge located on the other side of the tube should go up approximately the same amount. The instrumentation amplifier is a differential amplifier, and will amplify only the difference between the signals, which in the case of both gauges going up in value will cause the voltage at the gauge/ fixed resistor point junction to go down slightly. The gauge located on the other side of the tube will also increase in resistance, and the same thing will occur at its gauge/fixed resistor point. The instrumentation amplifier output will not change because there was no voltage differential.

Yet another benefit of the strain gauge amp configuration is the ability to produce signed values. This is necessary because the mathematics that calculates the forces and moments needs signed numbers to generate properly. Without signed values, off-center load cannot be properly calculated. Other calculations for forces and moments need signed values as well. The signed values are produced initially by the instrumentation amplifier, going both in the negative and positive quadrant.

As discussed, the output of the instrumentation amplifier 88 is fed to the programmable gain amplifier 102. This amplifier's gain is controlled by the microprocessor with 4 bits that make up the GAIN SELECT bus 104. This allows for the gain to be changed in 16 steps for gains of 1 to 100. The gain word/gain factor is linear. The overall gain for the strain gauges is equal to the gain product of the instrumentation amplifier and the programmable gain amplifier. The gain of the instrumentation amplifier is 50 and the gain of the programmable gain amplifier is 1 to 100, so the overall strain gauge gain is equal to 50 to 5,000.

Tri-axial inclinometers and accelerometers, depicted at block 106, provide signals to analog multiplexer 80. The actual part is MEMS technology with static as well as dynamic capability. The MEMS device has small weights attached to it so that it responds to the earth's gravity. In this way, it can be used as a tilt sensor, with the output relating to how the chip is positioned in relationship to the Earth's gravity.

The inclinometers and accelerometers may be included either in the housing itself, or in association with the limb. These inclinometers will provide a signal indicative of side-to-side and fore/aft motion of the limb and may be used in conjunction with strain gauge data to provide for a full range of motion analysis. The accelerometers will provide a signal indicative of acceleration and the direction of the limb's motion and may be used in conjunction with strain gauge sensor and inclination data to provide for a full range of motion analysis.

In yet other instances, measurement of the toe in/toe out position of the prosthetic foot relative to the remainder of the limb may be made, either by an onboard position sensor or by mechanical or other measurements made at the time that the limb is fitted. If the tilt sensors are located on the foot and on the limb, the microprocessor may analyze the signals and compute the angle between the foot and limb, thereby creating an electronic or 'virtual' goniometer. This analog multiplexer is addressed through path 84 with the same address lines as the strain gauge mux with the tilt mux output (110) going to a second A/D port pin located on the microprocessor so that no conflict with the strain gauge multiplexer is encountered.

The various components receive power from a rechargeable Li battery and an automatic switch to a super capacitor if the battery suddenly looses power. This condition will alert the data collection module (DCM) described later that the ITCA battery needs recharging, and will also send the last data available to the DCM. The battery voltage will be used by the various power supplies to produce the necessary voltages the ITCA needs, such as +10/+5V for the strain gauges, the +/−15 volts needed by the multiplexers, the +3.6V needed by the microprocessor.

USB communications is accomplished by connecting a UART/USB bridge chip 114 to the microprocessor UART port along path 116. A standard USB mini connector 118 is mounted on the ITCA PC board. The RF multi-channel transceiver 120 located on the ITCA communicates with the data collection module (DCM). The DCM will determine when the ITCA should transmit so that collisions do not occur. The ITCA performs signal averaging so that only necessary data transfer occurs. The multi-channel approach has been chosen so that multiple ITCAs can operate in the same space, and also to avoid being swamped by signals not associated with the ITCA/DCM.

Unaffected Limb Electronics Package (ULEP)

Figure 9:
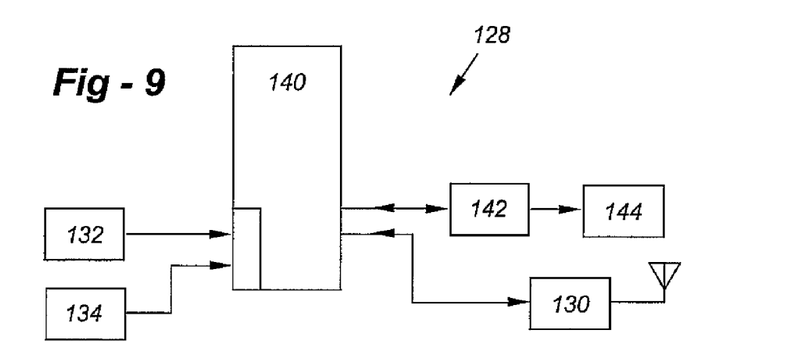
FIG. 9 is a simplified block diagram depicting an unaffected limb electronics package (ULEP) according to the invention.

FIG. 9 is a simplified block diagram depicting an unaffected limb electronics package (ULEP) generally at 128. The ULEP is connected to inclinometers/accelerometers 132, 134 that are mounted typically on the foot and on the limb or ITCA to measure both the ground surface tilt, and also the angle between the foot and the limb (virtual goinometer). The ULEP system is controlled by a separate processor 140. A USB translator 142 is interfaced to a USB port 144 for hardwired communication. In the normal mode of operation, only the RF transceiver link 130 to the DCM will be used.

Data Collection Module (DCM)

Figure 10:
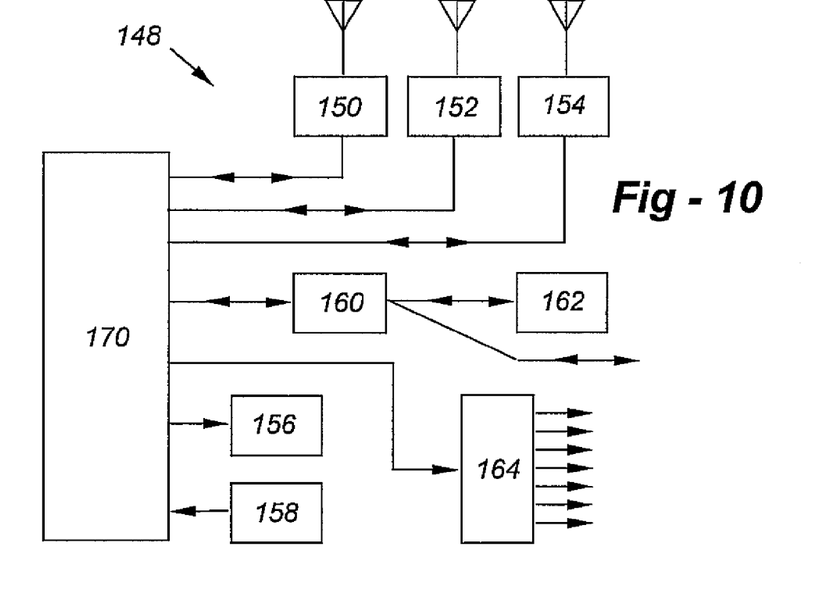
FIG. 10 is a block diagram of a data-collection module, or DCM, used for collecting the data from the ITCA(s), and the ULEP(s), as provided.

The data-collection module, or DCM, shown generally at 148 in FIG. 10, is used for collecting the data from the ITCA (s), and the ULEP(s), as provided. This is done over an RF Link using a transceiver 150 based upon low-power frequency hopping spread spectrum chips. With this technology, multiple units (multiple DCMs and their ITCA and ULEP) can be operated in the same radio space with little interference. The core of this technology is a frequency agile transmitter and receiver that change their frequency in a predictable method so that the entire system knows what the next frequency will be, and when to change. This RF link operates on the 915 MHz scientific and medical/short-range device (ISM/SRD) band.

The DCM is the master and assigns time slots for the ITCA and the ULEP to send their data to the DCM. This is called a deterministic system, which avoids collisions because of the strict rules regarding time slots. A second method of transmitting is clear-channel assessment (CCA) where the transceivers listen before transmitting so that they do not have two transmitters transmitting on the same frequency at the same time.

The DCM has optional BLUETOOTH, and/or 802.11b transceiver modules 152, 154 to transfer data the DCM gathered to PCs, PDAs, laptops and wireless hot spots. The data will be encrypted for security reasons. The optional modules will be turned on only when directed to do so by the person using the DCM. The reason for this is battery savings as well as security.

Time synchronization between the DCM and the two remotes (ITCA, ULEP) is critical because the forces, moments and angles need to be time stamped. Initially the DCM sends a time block to update the timing registers to permit time synchronization. The DCM and the remotes all have crystal clocks that are running at approximately the same frequency. However with an elapsed time of an hour (for instance), the clocks will drift. Periodically, the DCM will send a new absolute time block to the remotes so that time synchronization is maintained. Shorter time sync blocks will be sent by the DCM so that the remotes can make small adjustments to their clocks by updating a register that get incremented by a timer located in the CPU of the remote.

When the remotes upload their data to the DCM, an abbreviated time stamp will be sent. This will ensure that the DCM can associate a force, moment or tilt angle with time. This timing information will be extremely helpful to the researchers and prosthetist. If the DCM senses that a remote is having time problems, it will download a full absolute time block to that remote.

The DCM has a backlit LCD display 156 to monitor critical functions such as equipment degradation or impending failure. Also included is a beeper and a vibrator to alert the user. Other functions that can be displayed are battery life, remaining memory capacity, forces: average and peak, moments: average and peak, and tilt: average and peak. A keypad 158 enables the user to pick the various functions listed in the LCD section.

A USB 2.0 port 160 is available for connecting the DCM to a PC, PDA, MEMORY STICKS 162. Using the USB connection, a custom application program will upload the latest DCM data into a database and will allow the person to see how they are walking, if excessive forces were encountered. This program will show trends which will be beneficial to the user, the researcher and the prosthetist. Also available in this application will be select forces/select moments/select angles/select all; display average; display PEAKS; and display over-laid gate patterns (will ask how many steps).

For the gate labs, a 7-channel D/A port will be available for connecting the DCM directly to a data gathering system. This data will be 12 bit resolution analog signals that are single ended. A separate processor 170 provides system control functions. The DCM case has rounded edges so that it can fit into a pocket easily. A detachable clip can be used for attaching the DCM to a belt.

Intelligent Prosthetic Endo Component System (IPECS)

Figure 11:
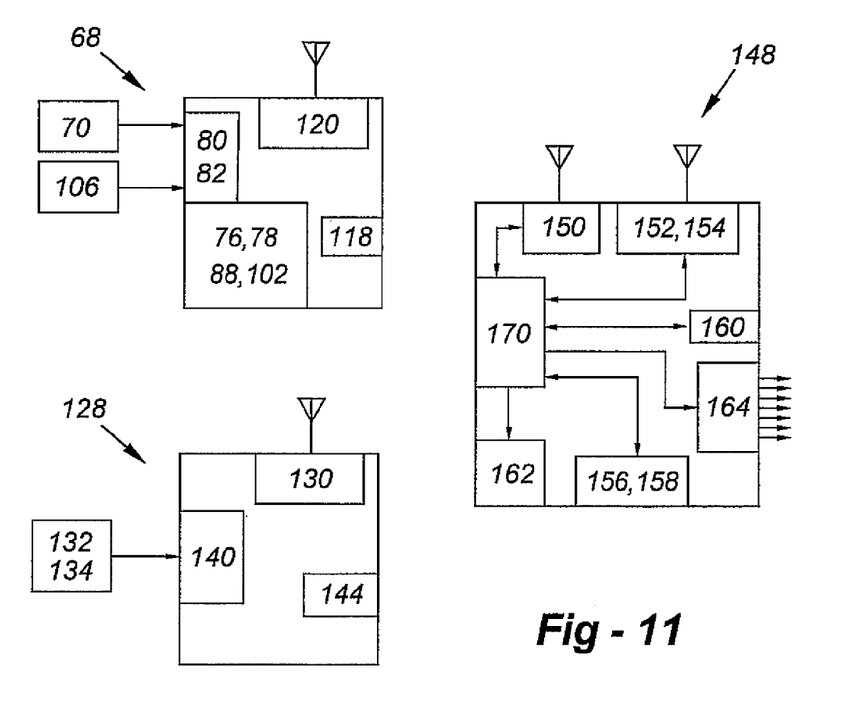
FIG. 11 is a diagram that shows how an ITCA and DCM may be used in conjunction with a ULEP to form an intelligent prosthetic endo component system (IPECS).

The ITCA and DCM may be used in conjunction with the unaffected limb electronics package (ULEP) to form an intelligent prosthetic endo component system (IPECS). FIG. 11 is a simplified block diagram showing one ITCA, one ULEP and one DCM. The system is composed of: one or two intelligent tube clamp adapters (ITCA), one ITCA if one ULEP used, one data collection module (DCM), and one or two unaffected limb electronics package (ULEP), one ULEP if one ITCA is used.

While the foregoing has been described primarily with reference to a system which is affixed to a prosthetic limb, similar systems may be affixed to prosthetic arms and the like. In view of the foregoing, numerous modifications and variations of the system will be apparent to those of skill in the art. The foregoing drawings, discussion and description are illustrative of specific embodiments, but they are not meant to be limitations upon the practice thereof. It is the following claims, including all equivalents, which define the scope of the invention.

Having described our invention, we claim:

1. A sensing system for use with a prosthetic limb, comprising:
    a support member configured for attachment to a prosthetic limb having a longitudinal axis;
    a plurality of sensor arrays disposed on the support member, each array including a plurality of strain gauge sensors, each sensor outputting an electrical signal responsive to loading imposed on the support member through the prosthetic limb;
    the plurality of sensor arrays including at least one array having a sensor aligned with the axis of the support member;
    electronic circuitry in communication with the gauges, the electronic circuitry being operative to receive the electrical signals from the strain gauges and provide a signal useful in the form, fit or function of the prosthetic limb;
    an inclinometer and accelerometer; and
    wherein the signal provided by the electronic circuitry is used to analyze the gait of a user.

2. A sensing system for use with a prosthetic limb, comprising:
    a support member configured for attachment to a prosthetic limb having a longitudinal axis;
    a plurality of sensor arrays disposed on the support member, each array including a plurality of strain gauge sensors, each sensor outputting an electrical signal responsive to loading imposed on the support member through the prosthetic limb;
    the plurality of sensor arrays including at least one array having a sensor aligned with the axis of the support member;
    electronic circuitry in communication with the gauges, the electronic circuitry being operative to receive the electrical signals from the strain gauges and provide a signal useful in the form, fit or function of the prosthetic limb;
    a pair of inclinometers, one disposed on either side of an articulating joint; and
    wherein the electronic circuitry is operative to receive signals from the inclinometers and output data approximating a goniometer.

3. The system of claim 2, wherein the inclinometers are disposed on either side of an ankle joint.

4. A sensing system for use with a prosthetic limb, comprising:
    a support member configured for attachment to a prosthetic limb having a longitudinal axis;
    a plurality of sensor arrays disposed on the support member, each array including a plurality of strain gauge sensors, each sensor outputting an electrical signal responsive to loading imposed on the support member through the prosthetic limb;
    the plurality of sensor arrays including at least one array having a sensor aligned with the axis of the support member;
    electronic circuitry in communication with the gauges, the electronic circuitry being operative to receive the electrical signals from the strain gauges and provide a signal useful in the form, fit or function of the prosthetic limb;
    a data collection module for receiving the signal from the electronic circuitry;
    an unaffected limb electronics package (ULEP) including an inclinometer and accelerometer; and
    wherein the module for collecting data is further operative to receive data from the inclinometer and accelerometer of the ULEP to analyze the gait of a user.

5. The system of claim 4, further including:
    an unaffected limb electronics package (ULEP) including a pair of inclinometers, one disposed on either side of an articulating joint; and
    wherein the module for collecting data is further operative to output data approximating that of a goniometer associated with the unaffected limb.

6. A sensing system for use with a prosthetic limb, comprising:
    a support member configured for attachment to a prosthetic limb having a longitudinal axis;

a plurality of sensor arrays disposed on the support member, each array including a plurality of strain gauge sensors, each sensor outputting an electrical signal responsive to loading imposed on the support member through the prosthetic limb;

the plurality of sensor arrays including at least one array having a sensor aligned with the axis of the support member;

electronic circuitry in communication with the gauges, the electronic circuitry being operative to receive the electrical signals from the strain gauges and provide a signal useful in the form, fit or function of the prosthetic limb;

wherein the electronic circuitry is powered by a generator associated with said prosthetic limb; and the generator is a piezoelectric generator or a moving magnet generator.

7. A sensing system for use with a prosthetic limb, comprising:

a support member configured for attachment to a prosthetic limb having a longitudinal axis;

a plurality of sensor arrays disposed on the support member, each array including a plurality of strain gauge sensors, each sensor outputting an electrical signal responsive to loading imposed on the support member through the prosthetic limb;

the plurality of sensor arrays including at least one array having a sensor aligned with the axis of the support member;

electronic circuitry in communication with the gauges, the electronic circuitry being operative to receive the electrical signals from the strain gauges and provide a signal useful in the form, fit or function of the prosthetic limb; and further including a motion detector operative to activate the electronic circuitry when motion is detected.

* * * * *